United States Patent [19]

Robbins et al.

[11] Patent Number: 5,334,376
[45] Date of Patent: Aug. 2, 1994

[54] COMPOSITIONS FOR CONDITIONING HAIR

[75] Inventors: Clarence R. Robbins, Martinsville; Amrit Patel, Dayton; Jane Clarke, Matawan, all of N.J.

[73] Assignee: Colgate-Palmolive Company, New York, N.Y.

[21] Appl. No.: 106,019

[22] Filed: Aug. 13, 1993

[51] Int. Cl.$^5$ .............................. A61K 7/06
[52] U.S. Cl. ........................ 424/70; 424/709
[58] Field of Search ............ 424/70, 709; 514/937, 514/951

[56] References Cited

U.S. PATENT DOCUMENTS

| | | | |
|---|---|---|---|
| 3,822,312 | 7/1974 | Sato et al. | 252/527 |
| 3,865,542 | 2/1975 | Kalopissis et al. | 8/101 |
| 3,890,434 | 6/1975 | Weisse et al. | 424/70 |
| 3,912,808 | 10/1975 | Sokol | 424/71 |
| 3,958,581 | 5/1976 | Abegg et al. | 132/7 |
| 3,966,903 | 6/1976 | Torii et al. | 424/71 |
| 3,973,574 | 8/1976 | Minagawa et al. | 132/7 |
| 4,070,320 | 1/1978 | Meyer-Stoll et al. | 260/29.4 |
| 4,243,659 | 1/1981 | Balingit et al. | 424/70 |
| 4,416,297 | 11/1983 | Wolfram et al. | 132/7 |
| 4,494,557 | 1/1985 | Nagel | 132/7 |
| 4,586,518 | 5/1986 | Cornwall et al. | 132/7 |
| 4,600,028 | 7/1986 | Edman et al. | 132/7 |
| 4,614,200 | 9/1986 | Hsiung et al. | 132/7 |
| 4,812,307 | 3/1989 | Siuta-Mangano | 424/71 |
| 4,832,950 | 5/1989 | Takaya et al. | 424/81 |
| 5,171,572 | 12/1992 | Suganuma et al. | 424/401 |

*Primary Examiner*—Thurman K. Page
*Assistant Examiner*—Jyothsna Venkat
*Attorney, Agent, or Firm*—Richard J. Ancel; Robert C. Sullivan

[57] ABSTRACT

A composition of particulate barium sulfate combined with one or more coreactants selected from the group consisting of a silicone free of amino groups, a long chain fatty alcohol and a long chain fatty acid amide has been found to be effective as a hair conditioner. The claimed compositions may also contain conventional surface-active agents, emulsifiers, stabilizers, and the like. In aqueous dispersion, these compositions impart improved body, manageability and style retention to hair.

20 Claims, No Drawings

COMPOSITIONS FOR CONDITIONING HAIR

BACKGROUND OF THE INVENTION

1. Field of the Invention

This invention relates to hair conditioning compositions. More particularly this invention relates to the use of barium sulfate in conjunction with certain silicone emulsions and/or long chain fatty alcohols or amides to impart improved body, manageability and style retention to hair.

2. Description of Related Art

Many patents have proposed solutions for the problem of hair management in disclosing compositions that build hair body and thickness by swelling the hair shafts. This swelling is achieved by reducing the cystine (—S—S—) linkage in the hair keratin to cysteine (—SH) linkages. However this leads to hair embrittlement and loss of hair tensile strength which must be compensated for.

Film-forming resins have been used to thicken hair but these make the hair so treated sticky and attract dirt.

U.S. Pat. No. 4,832,950 to Takaya et al. discloses the use of polyvalent metal salts of 2-mercaptopyridine-2-oxide as shampoo stabilizers. The polyvalent metals include magnesium, barium, strontium, zinc, tin, and zirconium with zinc as the preferred metal.

U.S. Pat. No. 4,586,518 to Cornwall et al. describes a hair fixative composition containing an aminoalkyl substituted polydiorganosiloxane.

U.S. Pat. No. 3,985,581 to Abegg et al. discloses a cosmetic preparation for strengthening hair that contains cationic polymers along with various divalent metal salts selected from the carbonate, silicate, nitrate, acetate, gluconate, pantothenate and lactate of calcium, magnesium, manganese, iron, strontium, zinc and cadmium.

U.S. Pat. No. 3,912,808 to Sokol relates to a hair waving composition that includes amino and quaternary ammonium polymers in conjunction with reducing agents capable of reducing the disulfide linkages in hair keratin.

U.S. Pat. No. 3,966,903 to Torii et al. relates to hair waving formulations including sulfites and calcium acetate.

U.S. Pat. No. 4,600,028 to Edman et al. relates to end wrap constructions saturated with a disulfide to control the action of mercaptan reducing agents used as permanent hair waving lotions.

U.S. Pat. No. 4,243,659 to Balingit et al. teaches the use of a solution of N,N-dimethyl urea, detergent and sodium bisulfite for permanently swelling hair.

It is an object of this invention to provide a hair conditioning composition that does not require chemical alteration of the hair.

It is another object of this invention to achieve hair conditioning without using strong reagents which may cause hair or skin damage.

It is still a further object to provide a post-shampoo treatment that removes a negative oily or limp feel from hair.

Other objects will become apparent to those skilled in the art upon a further reading of the specification.

SUMMARY OF THE INVENTION

A hair conditioning composition has been found that meets the objects enumerated above comprising particulate barium sulfate combined with one or more coreactants selected from the group consisting of a silicone free of amino groups, a long chain fatty alcohol and a long chain fatty acid amide.

Although the preferred combination of this invention comprises particulate barium sulfate plus a silicone free of amino groups, as a variation of this invention, the silicone may be combined with or replaced by a fatty alcohol or amide having about 12 to about 30 carbon atoms therein.

The claimed composition can be a water-based mixture containing emulsifying agents, including anionic, cationic and nonionic detergents, available commercially in conjunction with various inert materials, such as, fragrances, colorants, stabilizers and the like known to those skilled in the art.

DESCRIPTION OF THE PREFERRED EMBODIMENTS

The particle size of the barium sulfate component is not narrowly critical but is preferably less than about 10 um (microns). It is preferred to employ this component in a particle range of about 5 to about 0.01 um and even more preferred in a range of about 1.0 to about 0.1 um. The method of obtaining particulate barium sulfate is also not critical although there are many procedures that can be used. For example, it has been found convenient to mix aqueous solutions of sodium sulfate and barium acetate thus producing a precipitate of barium sulfate in finely divided form having a narrow particle size distribution with most of the particles below about 1.5 um. Barium sulfate purchased from commercial sources can also be used.

Although the concentration of barium sulfate used in the claimed composition is not critical, it is preferred that it constitute about 0.5 to about 5% by weight of the total formulation. A more preferred concentration lies in the range of about 1 to about 3% by weight of the total composition.

The preferred silicones used in this invention are alkylaryl polysiloxanes, dimethicones, cyclomethicones plus dimethiconols and the like. These silicones are all free of amino groups. It was unexpectedly found that aminosilicones are adsorbed too avidly on hair leaving the hair limp with little body, the opposite aim of the invention. Also the copolyols are too water soluble and do not provide the conditioning/roughness coverup effect necessary to provide an esthetically pleasing composition to the consumer. Representative useful silicones include Dow Corning 203 having a viscosity of 1200 cS, Union Carbide Corporation L-45 and Dow Corning 200 having viscosities in the range of 1000 to 60,000 cS, Dow Corning Q2-1241 fluid having a viscosity of 5000 sc, and the like. The concentration of silicone in these claimed compositions is about 5.0 to about 0.25% by weight of the total composition with a preferred range of about 1.0 to about 0.5% by weight.

While the silicone component can be combined with or replaced by a long chain fatty alcohol or amide having about 12 to about 30 carbon atoms, it is preferred to use an alcohol or amide having about 14 to about 20 carbon atoms. Cetyl alcohol is the most preferred member of this class. The concentration of this component can be about 10.0 to about 1.0% by weight based on the total composition, with a range of about 5.0 to about 2.0% being preferable. Other suitable alcohols include: lauryl, myristyl, palmityl, stearyl and arachidyl alcohols as well as tridecanol, pentadecanol, heptadecanol, nonadecanol, and the like at the same concentrations as specified above.

Suitable amides include primary alkyl amides, alkyl monoalkanol amides, alkyl diethanolamides and the like wherein the alkyl moieties have about 12 to about 20 carbon atoms.

While a wide latitude of emulsifying agents can be employed, it is preferred that the base shampoo contain anionic surfactants having about 12 to about 16 carbon atoms and cationic surfactants including alkyltrimethylammonium halides or alkyl dimethylammonium halides with one alkyl chain having about 12 to about 16 carbon atoms and nonionic emulsifiers including long chain esters or ethoxylated alcohols ($C_{16}$ or higher) or ethyoxylated sorbitan esters or combinations of these three emulsifiers.

As to physical properties of the total composition, it is preferred that the viscosity be in the range of about 3000–5000 cS as measured with a Brookfield Viscometer (spindle 4 at ambient temperature). However viscosities above and below this range can also be used. The pH range should preferably be about 6–8.

The accelerated shelf life of test compositions was measured by heating in an oven at 49° C. for 24 hours.

Hair body (volume) was evaluated either by trained panelists or by image analyzer measurements.

The trained panelists evaluated hair attributes (volume, texture, etc.) using their own personal experience criteria. For the most part, a panel of ten evaluators (five women and five men) was used. In some experiments this panel was supplemented by other assessors. "Visual" hair body was evaluated by panelists observing a tress from all directions. For "visual+feel" hair body assessments, panelists also touched the hair fibers while estimating body in the previously described manner.

For image analyzer measurements, a Zeiss Kontron Ibas 2000 image analyzer was used to obtain an instrumental measure of hair body. Hair tresses were measured by simply hanging the test tress next to standard (control) body (hair tress), capturing the images on the analyzer screen, and determining and recording the tress areas. (The same control body—a 30 g tress of Oriental hair, sprayed with hair spray until rigid—was used for all experiments). The camera used to capture images was a Sony XC-77CE miniature CCD video camera module with an Olympus 50-mm F2 auto-macro lens.

Hair body was evaluated as a ratio of the test tress area to the control area. An average of four images per stress (imaged at 90° to each other) was used for the assessment. This provides a "three dimensional" measurement of hair body, similar to a human assessment. Four images (and not two) were necessary, since the tress was rotated manually (exact angles of rotation cannot be verified) and not by an automated device. These measurements can be made rapidly; three minutes or less per tress, including setup.

Texture (roughness) of experimental hair samples was determined by trained panelists evaluations.

In practice the hair body composition is in the form of an aqueous emulsion of all of the components. A typical emulsion was prepared by dispersing a barium sulfate sol (2%) (premade by rapid mixing of solutions of barium acetate and sodium sulfate) in de-ionized water and heating to 85° C. with stirring. A preheated "oil" phase consisting of the surfactants Brij 72/Brij 721 (5%) and the emulsifier cocodiethanolamide (CDEA) (3%) was added with continued stirring followed by the silicone (1%). BRIJ 72 and BRIJ 721 are registered trademarks of ICI Americas Inc. for polyoxyethylene (2) stearyl ether and polyoxyethylene (21) stearyl ether respectively. The resultant stirred emulsion was then cooled to room temperature.

Representative hair treatment evaluations were carried out by shampooing long European hair tresses, rinsing and contacting them with compositions containing varying amounts of barium sulfate and silicone for one minute followed by a water rinse for one minute and finally drying. Image analyses of the tresses thus treated were then performed.

The invention is further described in the examples which follow. All parts and percentages are by weight unless otherwise specified.

EXAMPLE 1

Preparation of Hair Treatment Compositions

A 1 liter round-bottom flask fitted with a stirrer and thermometer was charged with de-ionized water and an aqueous solution containing barium sulfate and sodium acetate. The flask temperature was heated to 85° C. with stirring and then a preheated mixture of Brij 721, Brij 72, cocodiethanolamide, Union Carbide silicone L-45 (trade designation for trimethylsiloxy end blocked dimethylpolysiloxane having a Brookfield viscosity of 1000 cS with spindle 4) and preservative DMDM hydantoin, 1,3-dimethylol-5,5-dimethylhydantoin, added. The resultant emulsion was cooled to room temperature and used as such for the hair treatment experiments. The amounts charged are delineated in Table 1 as percentages of the total composition together with Control A. Example 1(a) contains barium and silicone L-45. Control A contains silicone L-45 but no barium sulfate. Example 1(b) contains barium sulfate but no silicone.

TABLE 1

| Ingredients | Control A | Example 1(a) | Example 1(b) |
| --- | --- | --- | --- |
| Deionized Water | 85.2 | 81.8 | 83.3 |
| Barium Sulfate | 0.0 | 2.0 | 2.0 |
| Sodium Acetate | 0.0 | 1.4 | 1.4 |
| Brij 721 | 5.0 | 5.0 | 5.0 |
| Brij 72 | 5.0 | 5.0 | 5.0 |
| Cocodiethanolamide | 3.0 | 3.0 | 3.0 |
| Silicone L-45 | 1.5 | 1.5 | 0.0 |
| DMDM Hydantoin | 0.3 | 0.3 | 0.3 |

The composition of Example 1 (a) was shown to be superior to either Example 1(b) or Control A by textural feel and ease of combing. Example 1(b) was judged by textural feel to have more body than Control A.

EXAMPLE 2

Preparation of Alternate Hair Treatment Composition

Using the equipment and method described in Example 1, an alternate hair treatment composition was prepared with the ingredients listed in Table 2 below. Timica Pearlwhite is a trade designation for a $TiO_2$/mica pearlescent mixture sold by the Mearl Co.

TABLE 2

| Ingredients | % |
| --- | --- |
| Deionized Water | 90.1 |
| Cetyl Alcohol | 3.0 |
| Barium Sulfate | 2.0 |
| Brij 721 | 1.5 |

TABLE 2-continued

| Ingredients | % |
| --- | --- |
| Brij 21 | 1.5 |
| Sodium Acetate | 1.4 |
| DMDM Hydantoin | 0.3 |
| Timica Pearlwhite (Mearl) | 0.2 |

The composition of Example 2, evaluated by textural feel and ease of combing, was found to have more body than Control A and combed easier than either Control A or Example 1 (b).

EXAMPLE 3

Hair Body Evaluations

A series of compositions (A through K) was prepared as in Example 1 with two different silicones, viz., Dow Corning 203 having a viscosity of 1200 cS and Dow Corning 1401, a mixture of cyclomethicone and dimethiconal having a viscosity of 5000 cS. Each of these compositions was applied to tresses of long European hair made by weighing and binding the hair with a rubber band followed by washing twice (one-minute wash; one minute rinse, 43° C.) with 20% ammonium lauryl sulfate surfactant to insure an initially clean fiber surface and combed twenty strokes to make sure that tresses were of uniform compatibility. After drying, the tresses were treated with one of the test compositions for thirty seconds followed by a thirty second rinse with deionized water. The data obained with the Image Analyzer (where Hair Body is given in arbitrary Units) for each of the treated tresses are delineated in Table 1 together with the amount of silicone and $BaSO_4$ deposited. These results show that as the amount of silicone in the compositions increases, the measured hair body generally decreases. Therefore for optimum hair body, the silicone level is preferably about 0.5% to about 1.0%.

TABLE 1

| Tress | % DC 203 | Hair Body | Barium |
| --- | --- | --- | --- |
| A | 0.5 | 0.795 | 0.55 |
| B | 1.0 | 0.777 | 0.41 |
| G | 1.5 | 0.655 | 0.50 |
| J | 2.0 | 0.645 | 0.57 |

| Tress | % DC 1401 | Hair Body | Barium |
| --- | --- | --- | --- |
| D | 0.5 | 0.696 | 0.57 |
| E | 1.0 | 0.689 | 0.81 |
| H | 1.5 | 0.671 | 0.70 |
| F | 2.0 | 0.683 | 0.66 |
| K | 3.0 | 0.626 | 0.71 |

DC 203 is a Dow Corning alkylaryl polysiloxane.
DC 1401 is a mixture of a cyclomethicone and dimethicone.

Although the invention has been described with a certain amount of particularity, it is understood that the present disclosure of the preferred forms has been made only by way of example and that numerous changes can be resorted to without departing from the spirit and the scope of the invention.

What is claimed is:

1. Hair conditioning composition comprising particulate barium sulfate combined with one or more coreactants selected from the group consisting of a silicone free of amino groups, a long chain fatty alcohol and a long chain fatty acid amide.

2. Composition as claimed in claim 1 wherein the particle size of the particulate barium sulfate is below about 5 microns.

3. Composition as claimed in claim 1 wherein the silicone is an alkylaryl polysiloxane.

4. Composition as claimed in claim 1 wherein the silicone is a mixture of cyclomethicone and dimethicone.

5. Composition as claimed in claim 1 wherein the silicone is a trimethylsiloxy end blocked dimethylpolysiloxane.

6. Composition as claimed in claim 1 in the form of an aqueous emulsion.

7. Composition as claimed in claim 6 containing about 0.5 to about 5.0 weight % of barium sulfate and about 0.25 to about 5.0 weight % of a silicone free of amino groups.

8. Composition as claimed in claim 6 containing a long chain fatty alcohol or long chain fatty acid amide having about 12 to about 30 carbon atoms.

9. Composition as claimed in claim 8 wherein the weight % of alcohol or amide is about 1.0 to about 10.0%.

10. Composition as claimed in claim 8 wherein the alcohol is cetyl alcohol.

11. Composition as claimed in claim 8 wherein the amide is cocodiethanolamide.

12. Method of conditioning hair which comprises contacting said hair with a composition comprising an aqueous dispersion of particulate barium sulfate combined with one or more coreactants selected from the group consisting of a silicone free of amino groups, a long chain fatty alcohol and a long chain fatty acid amide.

13. Method as claimed in claim 12 wherein the composition contains a silicone free of amino groups and a long chain fatty acid amide.

14. Method as claimed in claim 12 wherein the amount of barium sulfate is about 0.5 to about 5.0%, the amount of silicone is about 0.25 to about 5.0%, and the amount of long chain fatty acid amide is about 1.0 to about 10.0%, all based on the total dispersion weight.

15. Method as claimed in claim 12 wherein the silicone is an alkaryl polysiloxane.

16. Method as claimed in claim 12 wherein the silicone is a mixture of cyclomethicone and dimethicone.

17. Method as claimed in claim 12 wherein the silicone is a trimethylsiloxy end blocked dimethylpolysiloxane.

18. Method as claimed in claim 12 wherein the amide is cocodiethanolamide.

19. Method as claimed in claim 12 wherein the composition contains a fatty alcohol.

20. Method as claimed in claim 19 wherein the fatty alcohol is cetyl alcohol.

* * * * *